(12) United States Patent
Chen et al.

(10) Patent No.: US 9,983,182 B2
(45) Date of Patent: May 29, 2018

(54) DEVICE FOR SAMPLING AND DETECTING VOLATILE ORGANIC COMPOUNDS IN WATER

(71) Applicant: Rae Systems (Shanghai) Inc., Shanghai (CN)

(72) Inventors: Bing Chen, Shanghai (CN); Qian Zheng, Shanghai (CN)

(73) Assignee: RAE Systems (Shanghai) Inc., Shanghai (CN)

( * ) Notice: Subject to any disclaimer, the term of this patent is extended or adjusted under 35 U.S.C. 154(b) by 15 days.

(21) Appl. No.: 14/395,576

(22) PCT Filed: Jun. 28, 2013

(86) PCT No.: PCT/CN2013/078310
§ 371 (c)(1),
(2) Date: Oct. 20, 2014

(87) PCT Pub. No.: WO2014/000685
PCT Pub. Date: Jan. 3, 2014

(65) Prior Publication Data
US 2015/0082864 A1    Mar. 26, 2015

(30) Foreign Application Priority Data

Jun. 29, 2012   (CN) .......................... 2012 1 0223247
Jun. 29, 2012   (CN) ..................... 2012 2 0313875 U (51) Int. Cl.
*G01N 1/22*      (2006.01)
*G01N 33/00*    (2006.01)
(Continued)

(52) U.S. Cl.
CPC ....... *G01N 33/0047* (2013.01); *G01N 1/2202* (2013.01); *G01N 1/4055* (2013.01);
(Continued)

(58) Field of Classification Search
CPC ........... G01N 33/0047; G01N 33/1826; G01N 1/2202; G01N 1/4055; G01N 2001/4066; G01N 2030/025
(Continued)

(56) References Cited

U.S. PATENT DOCUMENTS 3,387,487 A * 6/1968 Hodges, Jr. ............... G01N 7/14
73/19.1
3,617,470 A * 11/1971 Schlinger ............... C10G 1/065
201/20
(Continued)

FOREIGN PATENT DOCUMENTS

CN          101126687 A        2/2008
CN          201060109 Y        5/2008
(Continued)

OTHER PUBLICATIONS

Murata A. et al. "Continuous Analyzer for Volatile Organic Compounds in Air and Water" http://www.yokogawa.com/rd/pdf/TR/rd-tr-r00031-001.pdf; Yokogawa Technical Report English Edition, No. 31, 2001, pp. 1-4.
(Continued)

*Primary Examiner* — Benjamin Schmitt
(74) *Attorney, Agent, or Firm* — Wick Phillips Gould & Martin LLP (57) ABSTRACT

The present invention discloses a sampling and detection device for detecting volatile organic content in water, comprising a hollow sampler (3) and a gas detector (2) connected to the sampler (3). A side wall of a lower half of the sampler (3) is provided with more than one water inlet channel (1), and a lower end is provided with a gas bubbler (10). Said detection device ensures measurement accuracy and continuity while facilitating in-situ detection.

18 Claims, 2 Drawing Sheets

(51) Int. Cl.
*G01N 1/40* (2006.01)
*G01N 30/02* (2006.01)
*G01N 33/18* (2006.01)

(52) U.S. Cl.
CPC ......... *G01N 30/02* (2013.01); *G01N 33/1826* (2013.01); *G01N 2001/4066* (2013.01); *G01N 2030/025* (2013.01)

(58) Field of Classification Search
USPC .................................. 73/19.12, 28.04, 31.07
See application file for complete search history.

(56) References Cited

U.S. PATENT DOCUMENTS

| | | | | |
|---|---|---|---|---|
| 4,330,385 | A | * | 5/1982 | Arthur ............... G01N 33/1806 204/409 |
| 5,222,032 | A | * | 6/1993 | Fleming ............. G01N 33/0049 700/271 |
| 5,421,194 | A | * | 6/1995 | Doyle ...................... G01N 1/40 73/19.01 |
| 5,448,922 | A | | 9/1995 | Kimbell et al. |
| 5,620,593 | A | * | 4/1997 | Stagner ............. B01D 19/0005 166/372 |
| 5,773,713 | A | | 6/1998 | Barber et al. |
| 5,831,143 | A | * | 11/1998 | Galloway ............... G01N 30/12 422/78 |
| 6,306,296 | B1 | * | 10/2001 | Kerfoot ............... B01F 3/04262 210/170.07 |
| 2001/0003426 | A1 | | 6/2001 | Matter et al. |
| 2009/0007635 | A1 | | 1/2009 | Zamfes |
| 2011/0094105 | A1 | | 4/2011 | Tatsumi et al. |

FOREIGN PATENT DOCUMENTS

| | | |
|---|---|---|
| CN | 201561885 U | 8/2010 |
| CN | 202008464 U | 10/2011 |
| CN | 102305729 A | 1/2012 |
| CN | 102323115 A | 1/2012 |
| CN | 102353560 A | 2/2012 |
| CN | 102721579 A | 10/2012 |
| CN | 202735137 U | 2/2013 |
| EP | 0256444 A1 | 2/1988 |
| EP | 0256444 A2 | 2/1988 |
| EP | 2833117 A1 | 2/2015 |
| JP | 1-191036 | 8/1989 |
| JP | 3466503 B2 | 8/2003 |
| JP | 3466503 B2 | 11/2003 |
| WO | 2014000685 A1 | 1/2014 |

OTHER PUBLICATIONS

EP138095542, Extended European Search Report, dated Oct. 2, 2015 8 pages.
Search Report for priority WO Application PCT/CN2013/078310, dated Sep. 19, 2013 (with English-language translation).
International Application No. PCT/CN2013/07831, Written Opinion of the International Searching Authority, dated Sep. 19, 2013, 13 pages.
International Application No. PCT/CN2013/07831, International Preliminary Report on Patentability, dated Dec. 31, 2014, 6 pages.
China Patent Application No. 201210223247.0, First Search Report, dated Sep. 4, 2013, 2 pages.
China Patent Application No. 201210223247.0, Office Action, dated Sep. 16, 2013, 13 pages.
China Patent Application No. 201210223247.0, Office Action, dated Apr. 25, 2014, 11 pages.
China Patent Application No. 201210223247.0, Notification to Grant Patent Right dated Nov. 4, 2014, 4 pages.

* cited by examiner

DEVICE FOR SAMPLING AND DETECTING VOLATILE ORGANIC COMPOUNDS IN WATER

FIELD OF THE INVENTION

The present invention relates to the field of detection instruments, in particular to a sampling and detection device for detecting volatile organic content in water.

BACKGROUND OF THE INVENTION

Various volatile organic compounds may enter into the environment water bodies such as surface water, ground water, seawater etc. and the production and living water in many ways such as by means of emission, leakage or diffusion etc. The volatile organic compounds will impose unfavorable influence on or potential threat to environment, ecology, safety and health etc. depending on their different properties. Various organic compounds such as aromatic hydrocarbon, aliphatic hydrocarbon and halogenated hydrocarbon are not easily decomposed due to their stable chemical properties. They will penetrate into groundwater aquifers and cause serious destruction to the environment. Long-term contact with such organic compounds will result in human chronic poisoning, induce cancer and also have a direct influence on the reproductive system and nervous system. Therefore, monitoring of the volatile organic pollutants in water gets increasingly important in environment analysis work. The causes for water pollution includes improper treatment of industrial waste water, improper treatment of household garbage, leakage events of petroleum chemical plants and leakage events of ships at sea. As for some leakage events, urgent measures must be taken to cut off the spread of pollution as quickly as possible. Therefore, it is extremely important to quickly determine the pollution situations of the water body. The conventional manner by sampling polluted water source and bringing the sample back to a laboratory for detection obviously cannot deal with various sudden events, and some portable detection instruments usually have disadvantages such as undesirable accuracy of measurement result, high cost of the instrument and inconvenient for carrying.

The difficulty in detecting volatile organic compound (VOC) in water body lies in in-situ sampling and quick analysis. The conventional sampling manner is generally as follows, i.e. after sampling in a vessel, sending it to a laboratory for extraction (e.g., as disclosed in US patent application US2011/094105 A1), enrichment (e.g., as disclosed in US patent application US2001/0003426A1) or purging-and-trapping methods and the like. Obviously, these methods cannot meet the requirements for in-situ test, and the components of the water body inevitably change to some extent due to a longer time interval delayed from sampling to testing. In addition, the subsequent processes such as extraction, enrichment and purging-and-trapping etc. are complicated, quite time consuming and cannot completely reflect/indicate the actual water sample components. Collecting the volatile gas in water by using a headspace method is obviously superior to the situation by using the above sampling method. The U.S. Pat. No. 5,773,713 disclosed the use of a detection method in which a polymer membrane is placed in the detected water sample, VOCs in the water permeate or diffuse through the polymer membrane and are brought out by a dilution gas stream for detection. The U.S. Pat. No. 5,448,922 discloses a gas permeation system which also uses a gas permeation membrane. The method of using a membrane for separation is disadvantageous in that flow of the gas depends on properties of the membrane to a great extent, and is substantially affected by the material, length and cross-sectional area of the membrane and greatly affected by the pressure of the system. Therefore, the reliability is not so high and the structure is so complicated. It can be seen that up to date there is no such a device for efficiently, quickly, portably and reliably in-situ detecting the volatile organic pollutants in water.

SUMMARY OF THE INVENTION

In view of the above-mentioned drawbacks in the prior art, the object of the present invention is to provide a device for efficiently, quickly, portably and reliably detecting the volatile organic content in water.

In the first aspect of the present invention, a sampling and detection device for detecting volatile organic content in water is provided, the device comprising a hollow sampler and a gas detector connected to the sampler. The side wall of a lower half of the sampler is provided with more than one water inlet channel, and the lower end is provided with a gas bubbler.

The gas bubbler functions to enable the purge gas entering a cavity to be divided into one or more tiny gas bubbles. The gas bubbler may be one or a group of pores or a porous material.

The water inlet channel is small enough so that gas bubbles cannot escape therefrom. These water inlet channels can also be replaced with a slit having a width ranging from 0.1 mm to 5 mm or a mesh plate with a certain pore structure, which can perform the same function. The pore area of the water inlet channel should amount to 3 $mm^2$ or higher so that the water body in the sampler can exchange with to-be-detected water body outside the sampler in time, so as to ensure the precision of the measurement result.

Preferably, the device further comprises a gas inlet pipe, a gas outlet pipe and a purge gas intake pump. One end of the gas inlet pipe is communicated with a bottom of the sampler and the other end is connected to the purge gas intake pump. One end of the gas outlet pipe is communicated with a top of the sampler and the other end is connected to the gas detector.

Preferably, the gas outlet pipe is provided with a gas sample collection pump.

Preferably, the gas inlet pipe is further provided with a purge gas purifier. The purge gas purifier is a filter filled with an adsorbing agent and is used to remove the impurities in the purge gas. When the purge gas itself is confirmed as clean gas that does not affect detection, the purge gas purifier may be omitted. The gas outlet pipe is made of a material such as Teflon that does not adsorb an organic volatile gas, such that detected concentration is not reduced or detection time is not delayed because the gas sample is not adsorbed while passing through the pipe, and the next detection result is not affected by desorption of the volatile organic compound adsorbed upon previous detection.

Preferably, the gas outlet pipe is further provided with a gas sample dehumidifier. The gas sample dehumidifier is formed by a casing pipe or laminated tube, wherein the outer tube or the outer layer is made of a gas impermeable sealing material and an inner tube or inner layer is made of a material which only allows water molecules to permeate, such as Nafion, and a water absorbent material such as silica gel is filled between the inner and outer tubes or between inner and outer layers. The gas sample flows through the inner tube or inner layer, wherein a part of the water molecules permeate the selectively permeable material of the inner tube or inner layer and is adsorbed by the water absorbent material filled between the inner and outer tubes or filled between the inner and outer layers, thereby the relative humidity of the gas sample flowing through the inner tube or inner layer drops/fills/is reduced. When the relative humidity does not exert an influence on the whole sampling and detection system, the gas sample dehumidifier may be omitted.

Preferably, the gas bubbler is disposed at a location where the gas inlet pipe is communicated with the sampler.

Preferably, the water inlet channel is a pore or a slit, wherein the pore has a diameter of 0.1-5 mm, and the slit is 0.1-1000 mm long and 0.1-5 mm wide.

Preferably, the lower half of the sampler is 3-100 cm high.

Preferably, the gas detector is selected from a group consisting of a photoionization detector (PID), a thermal conductivity detector (TCD), a hydrogen flame detector, an ion mobility detector, a mass spectrometry detector and a spectral detector. The gas detector mainly functions to identify the components in the purge gas.

Preferably, at an inlet end of the gas detector is further provided with a gas separating means which is selected from a gas chromatographic column. Before entering the gas detector, the purge gas needs to pass through the gas separating means first whereby components of the gas are separated such that the component VOCs in the purge gas enter the gas detector one by one, so as to improve the detection precision of the gas detector.

Preferably, at least one float is further provided on the outer wall of the upper half of the sampler.

The at least one float mainly functions to allow the lower half of the sampler completely under a liquid surface of the detected water body and keep the cavity remain vertical (or substantially vertical), and mainly functions to form a gas sample collection chamber within the upper half of the sampler.

Preferably, the sampler is of the structure of a hollow column-shaped cavity. The at least one float is on the same horizontal section of the column-shaped cavity structure. The cross-sectional area of the column-shaped cavity is 1 $cm^2$-1 $m^2$, and the ratio of the height of the lower half of the sampler to the total height of the sampler is ¼-9/10.

Preferably, a gas path from the gas sample collection chamber of the sampler to the gas detector is completely hermetically isolated from the external environment, and the resistance of the gas from the inlet to the outlet is relatively small.

Preferably, the gas detector is further communicated with the purge gas intake pump, and a closed loop is formed between the gas inlet pipe, the sampler, the gas outlet pipe and the gas detector.

Preferably, the gas detector is further communicated with the purge gas intake pump. The purge gas intake pump is integrated with a gas sample collection pump. A closed loop is formed between the gas inlet pipe, the sampler, the gas outlet pipe and the gas detector. After passing through the gas sample collection pump, the gas sample dehumidifier and the gas separating means, the purge gas in the sampler enters the gas detector and flows out of the gas detector after detection, reaches the purge gas intake pump via the pipeline, then enters the gas inlet pipe again after passing through the purge gas intake pump, and then enters the sampler again after passing through the purge gas purifier, thereby achieving the closed circulation of the whole gas pipeline. The purge gas intake pump is replaced with a gas pump carried in the gas detector. The whole device, after the integration, is made more compact and smaller.

In the second aspect of the present invention, a method for detecting volatile organic content in water by using the above sampling and detection device for detecting volatile organic content in water is provided, the method comprising the following steps:

1) placing the sampler in the to-be-detected water body, introducing the purge gas into the sampler and then into the gas detector for detection;

2) obtaining concentration of volatile organic compounds in the to-be-detected water body according to detection results obtained by the gas detector and a standard sample concentration curve.

Preferably, step 1) is: placing the sampler in the to-be-detected water body, using the purge gas intake pump to introduce the purge gas into the sampler via the inlet pipe, and then into the gas detector for detection via the gas outlet pipe.

Preferably, the purge gas flow of the gas inlet pipe is controlled slightly greater than or equal to the purge gas flow of the gas outlet pipe, such that the gas flow entering the cavity of the sampler is made greater than or equal to the gas flow pumped from the gas sample collection chamber within the cavity of the sampler.

Preferably, the gas flow in the gas inlet pipe is controlled in a range from 1 ml/min to 10 L/min, and a volume of the water entering the sampler is controlled in a range of 1 ml-1000 L.

The volume of the water entering the sampler varies in response to the height and cross-sectional area of a lower segment of the sampler.

The design is carried out to ensure that the gas in the gas sample collection chamber will not decrease gradually such that the liquid surface rises and even the liquid is sucked into the gas sample outlet pipe, the gas sample dehumidifier and the gas detector. When the gas intake flow at the bottom of the sampler is equal to the gas exhaust flow at the top, the liquid surface in the cavity of the sampler keeps stable. When the gas intake flow at the bottom of the sampler is greater than the gas exhaust flow at the top, the surplus gas enables the liquid surface in the cavity of the sampler to drop to the position of the lower segment of the sampler with pores or slits and thereby escape out of the cavity of the sampler. However, at this time, a procedure of pumping the gas sample from the top of the gas sample collection chamber is not affected. When the flow of the purge gas pump is much greater than the flow of the gas collection pump, partial flow may be branched out from the purge gas inlet pipe.

Preferably, the purge gas is selected from nitrogen, air and inert gases.

Preferably, the purge gas purges the to-be-detected water body in the sampler for 5 seconds-10 minutes (which is a balancing time), and then the gas detector is started for detection (or the detector is started before the purging, and data are read after the data obtained from the purging gets balanced).

Preferably, the purge gas is further subjected to purification treatment before entering the sampler, and subjected to bubbling treatment upon entering the sampler, and further subjected to dehumidification treatment and gas separation treatment after flowing out of the sampler and before entering the gas detector.

The gas separation treatment is accomplished by means of gas separating means such as a gas chromatographic column located at an inlet end of the detector.

The purification treatment is accomplished by means of the purge gas purifier located on the gas inlet pipe.

The bubbling treatment is accomplished by means of a gas bubbler at a location where the gas inlet pipe is communicated with the sampler.

The dehumidification treatment is accomplished by means of a gas sample dehumidifier located on the gas outlet pipe.

The principles of the device and method for detecting volatile organic content in water according to the present invention are as follows: the purge gas blown out of the bottom of the sampler is subjected to the bubbling treatment, the bubbles carry the volatile organic compounds in the detected water and gather in the gas sample collection chamber at the upper segment of the sampler, first enter the gas sample dehumidifier for dehumidification and then enter the gas detector for concentration detection. Gas sealing means are provided at respective interfaces. According to the design of the present invention, the concentration of the volatile gas carried out of the detected water by the bubbling of the purge gas approximates to the headspace gas-liquid balance concentration and in an approximately linear relationship with its content in the water. Before experimentation, the standard sample of the desired VOC concentrations needs to be detected to determine the linear relationship between the VOC gas detection value and the actual concentration. Upon actual detection, the concentration of the volatile organic compounds in the to-be-detected water body can be obtained by converting from the detection value thereof. The lower detecting limit of the device of detecting volatile organic pollutants in the water according to the present invention can be in the range of μg/L level or even lower.

After experimentation, the inventor finds that the detection device as well as the sampling and detection method for volatile organic content in water according to the present invention have the following advantageous effects: it is not necessary to take out a water sample and the sampler may be directly placed in water such that the volatile organic compounds in water may be sampled and then enter the connected detector for detection; water in the cavity freely exchanges with the water in the water body all the time so that the concentration of the detected volatile organic compounds will not reduce along with the successive extraction due to the sampling and thereby the measurement accuracy and continuity is ensured.

LISTING OF PARTS 1 water inlet channel
2 gas detector
3 sampler
4 gas inlet pipe
5 gas outlet pipe
6 purge gas intake pump
7 gas sample collection pump
8 purge gas purifier
9 gas sample dehumidifier
10 gas bubbler
11 float
12 gas sample collection chamber
13 gas sample outlet

DETAILED DESCRIPTION OF PREFERRED EMBODIMENTS

Embodiments of the present invention are described by the following specific examples. Those skilled in the art can easily understand other advantages and effects of the present invention from the content disclosed by the description. The present invention may also be implemented or applied through other different specific embodiments. Details in the description may be modified or altered on basis of different opinions and application without departing from the spirit of the description.

Figure 1:
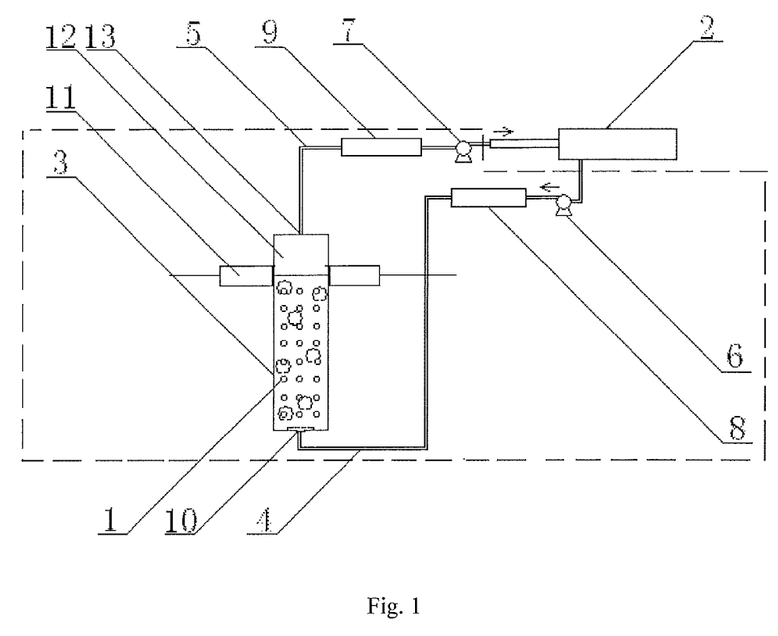
FIG. 1 is a schematic structural view of a sampling and detection device for detecting volatile organic content in water according to the present invention.
Figure 2:
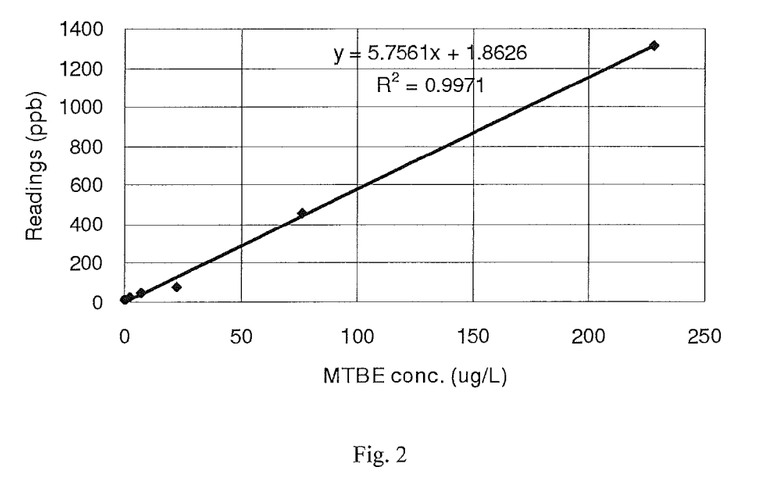
FIG. 2 is a linear diagram schematically showing the detection result of methyl tert-butyl ether (MTBE) in water according to the present invention.
Figure 3:
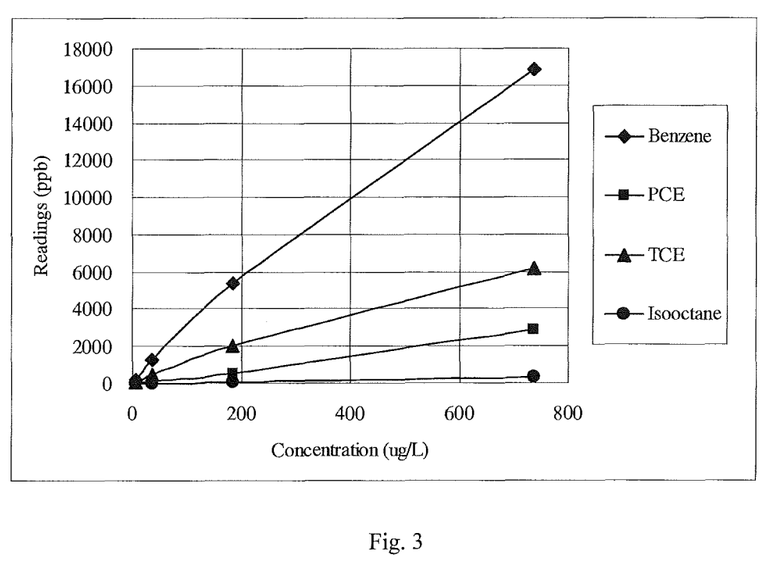
FIG. 3 is a linear diagram schematically showing the detection result of other types of VOCs in water according to the present invention.

Reference is made to FIG. 1 through FIG. 3. It should be noted that, figures provided by the embodiments only illustratively present the basic ideas of the present invention, so the figures are only drawn with assemblies related to the present invention not with the number, shape and size of assemblies upon actual implementation. Upon actual implementation, the shape, number and scale of assemblies may vary randomly and the layout of the assemblies may be more complicated.

FIG. 1 illustrates a sampling and detection device for detecting volatile organic content in water, the device comprising a hollow sampler 3 and a gas detector 2 connected to the sampler 3. The side wall of a lower half of the sampler 3 is provided with more than one water inlet channel 1, and a lower end is provided with a gas bubbler 10.

The water inlet channel 1 is small enough such that gas bubbles cannot escape therefrom. These water inlet channels can also be replaced with a mesh plate with a certain pore structure, which can perform the same function.

The gas bubbler 10 functions to enable a purge gas entering a cavity to be divided into one or more tiny gas bubbles. The gas bubbler 10 may be one or a group of pores or a porous material. Dividing the purge gas into tiny gas bubbles can increase gas-liquid contact area of the gas entering the sampler, improve the concentration of VOCs in the purge gas and make the detection result more precise.

Specifically, the device further comprises a gas inlet pipe 4, a gas outlet pipe 5 and a purge gas intake pump 6. One end of the gas inlet pipe 4 is communicated with a bottom of the sampler 3 and the other end is connected to the purge gas intake pump 6. One end of the gas outlet pipe 5 is communicated with a top of the sampler 3 and the other end is connected to the gas detector 2.

Specifically, the gas outlet pipe 5 is provided with a gas sample collection pump 7.

Specifically, the gas inlet pipe 4 is further provided with a purge gas purifier 8. The purge gas purifier 8 is a filter filled with an adsorbing agent and used to remove impurities in the purge gas. When the purge gas itself is confirmed as clean gas that does not affect detection, the purge gas purifier may be omitted. The gas outlet pipe is made of a material such as Teflon that does not adsorb an organic volatile gas, such that the detected concentration is not reduced or detection time is not delayed because the gas sample is not adsorbed while passing through the pipe, and the next detection result is not affected by desorption of the volatile organic compound adsorbed upon the last detection.

Specifically, the gas outlet pipe 5 is also provided with a gas sample dehumidifier 9. The gas sample dehumidifier 9 is formed by a casing pipe or laminated tube, wherein the outer tube or the outer layer is made of a gas impermeable sealing material and an inner tube or inner layer is made of a material which only allows water molecules to permeate, such as Nafion, and a water absorbent material such as silica gel is filled between the inner and outer tubes or between inner and outer layers. The gas sample flows through the inner tube or inner layer, wherein a part of the water molecules permeate the selectively permeable material of the inner tube or inner layer and is adsorbed by the water absorbent material filled between the inner and outer tubes or filled between the inner and outer layers, thereby the relative humidity of the gas sample flowing through the inner tube or inner layer drops/falls/is reduced. When the relative humidity does not exert an influence on the whole sampling and detection system, the gas sample dehumidifier may be omitted.

Specifically, the gas bubbler 10 is disposed at a location where the gas inlet pipe 4 is communicated with the sampler 3.

Specifically, the water inlet channel 1 is a pore or a slit, wherein the pore is of a circular shape. The pore has a diameter of 0.1-5 mm, and the slit is 0.1-1000 mm long and 0.1-5 mm wide. The water inlet channel on the sampler is small enough such that gas bubbles cannot escape therefrom. These water inlet channels may be replaced with a slit with a width ranging between 0.1-5 mm or a mesh plate with a certain pore structure, which can perform the same function. The pore area of the water inlet channel should amount to 3 $mm^2$ or more so that the water body in the sampler can exchange with the to-be-detected water body outside the sampler in time to ensure the precision of the measurement result.

Specifically, the lower half of the sampler 3 is 3-100 cm high.

Specifically, the gas detector 2 is selected from a group consisting of a photoionization detector, a thermal conductivity detector, a hydrogen flame detector, an ion mobility detector, a mass spectrometry detector and a spectral detector. The gas detector 2 mainly determines the gas components and content of the purge gas entering the detector and may output a qualitative or quantitative detection result respectively for components and/or content of the gas according to the type of the specifically-selected gas detector.

Specifically, an inlet end of the gas detector 2 is further provided with a gas separating means which is selected from a gas chromatographic column. Before entering the gas detector 2, the purge gas needs to pass through the gas separating means first whereby components of the gas are separated so that component VOCs in the purge gas enter the gas detector 2 successively to improve the detection precision of the gas detector 2.

Specifically, at least one float 11 is further provided on the outer wall of the upper half of the sampler 3. The float 11 can keep the sampler 3 vertical (or substantially vertical) so that the lower half of the sampler 3 is completely under a liquid surface of the detected water, a stable gas sample collection chamber is formed in the upper half of the sampler 3, the liquid surface in the cavity of the sampler 3 and a total amount of the water in the cavity of the sampler 3 are maintained stable.

Specifically, the sampler 3 is of the structure of a hollow column-shaped cavity. The at least one float 11 is on the same horizontal section of the column-shaped cavity structure. The cross-sectional area of the column-shaped cavity is 1 $cm^2$-1 $m^2$, and the ratio of a height of the lower half of the sampler 3 to a total height of the sampler is ¼-9/10.

Specifically, the gas detector 2 is further communicated with the purge gas intake pump, and a closed loop is formed between the gas inlet pipe, the sampler, the gas outlet pipe and the gas detector.

Specifically, when the device is in an ideal state, the gas intake flow at the bottom of the sampler is equal to the gas exhaust flow at the top of the sampler. The gas path from the gas sample collection chamber 12 of the sampler 3 to the gas detector 2 is completely hermetically isolated from the external environment, and the resistance of the gas from the inlet to the outlet is relatively small. The smaller resistance ensures that the gas pressure in the sample collection chamber in the cavity does not vary greatly such that the VOC content in the purge gas does not vary with the gas pressure, the liquid surface within the cavity of the sampler remains stable and the measurement results gets more precise. When the gas intake flow at the bottom of the sampler is greater than the gas exhaust flow at the top, the surplus gas enables the liquid surface within the cavity of the sampler to drop to a position of the lower segment of the sampler with pores or slits and thereby escape out of the cavity of the sampler. However, at this time, a procedure of pumping the gas sample from the top of the gas sample collection chamber is not affected. When the flow of the purge gas pump is much greater than the flow of the gas collection pump, partial flow may be branched out from the purge gas inlet pipe.

Specifically, the purge gas intake pump is replaced with a gas pump carried in the gas detector. The purge gas intake pump 6 is integrated with gas sample collection pump 7, and their function is performed by the same gas pump in the photoionization detector. The purge gas is not provided from a dedicated steel cylinder gas, and directly employs the purified air in the pipe so that the whole device is light-weighted and compact and can be portably carried to waters suspected to be polluted or already confirmed polluted to detect the concentration of the organic volatile pollutants therein. The whole gas pipeline is a closed loop. The purge gas in the sampler 3, after passing through the gas sample collection pump 7, the gas sample dehumidifier 9 and the gas separating means, enters the gas detector 2 and flows out of the gas detector 2 after detection, reaches the purge gas intake pump 6 via the pipeline, then enters the gas inlet pipe 4 again after passing through the purge gas intake pump 6, and then enters the sampler 3 again after passing through the purge gas purifier 8, thereby achieving the closed circulation of the whole gas pipeline. The whole device, after the integration, is made more compact and smaller.

When the sampling and detecting device according to the invention is used to detect the volatile organic content in water, a standard sample concentration curve is drawn first. The standard sample concentration curve may be obtained by the following method:

1) formulating a standard sample solution: formulating various VOCs respectively into water solution with a gradient concentration;

2) detecting the standard sample solution: using the above sampling and detecting device to detect VOC content in the standard sample solution formulated in step 1);

3) drawing a standard curve: drawing a standard sample concentration curve with the concentration of the formulated standard sample solution as horizontal coordinate and with the VOC content in the respective standard sample solutions detected in step 2) as longitudinal coordinate.

Gases that may be detected according to the present invention comprise volatile organic gases such as methyl tert-butyl ether, benzene, tetrachloroethylene, trichloroethylene, vinyl acetate and isooctane.

The VOC concentration in the to-be-detected water body is in a range of $0.1$-$10^6$ µg/L.

Detection Example 1

Detection of Methyl Tert-Butyl Ether (MTBE) in Water

As shown in FIG. 1, the photoionization detector is used as the gas detector, the gas detector is a hand-held type, the sampler is of a cylindrical shape, the float is the fixing means of the sampler and located at ⅔ of the total height of the sampler, the water inlet channel is of a circular shape with a diameter in a range of 0.1-5 mm.

The gas flow in the gas inlet pipe is controlled as 100-500 ml/min, and the volume of water entering the sampler is controlled as 300-800 ml. The purge gas flow of the gas inlet pipe is slightly greater than or equal to the purge gas flow of the gas outlet pipe, the purge gas is subjected to purification treatment and bubbling treatment before being introduced into sampler, and is subjected to gas dehumidification treatment and separation treatment before being introduced into the gas detector. The purge gas purges the to-be-detected water body in the sampler for 0.5-3 minutes, and then the gas detector is started for detection.

Table 1 lists the corresponding results when a sample machine is used to detect methyl tert-butyl ether (MTBE) in a standard sample water body. The test is performed in a water pool of a laboratory. After the detecting device gets ready, the formulated MTBE solution is poured into the water pool, the sampler is placed in the water pool for detection, each standard sample is read three times, the reading detected by PID is VOC concentration in the gas entering the gas detector with a measure unit of ppb. The exhibits an excellent linear relationship when used to detect low-concentration (7.4 µg/L) MBTE.

TABLE 1

| Conc. µg/L | Reading (PID reading) | | | | STDEV, % | ppb/(µg/L) |
|---|---|---|---|---|---|---|
| | Test 1 | Test 2 | Test 3 | average | | |
| 0 | 0 | 0 | 0 | 0 | — | — |
| 7.41 | 48 | 71 | 58 | 59 | 20 | 8.0 |
| 37.04 | 265 | 380 | 317 | 321 | 18 | 8.7 |
| 185.18 | 1564 | 1965 | 1701 | 1743 | 12 | 9.4 |
| 740.70 | 6276 | 7305 | 6424 | 6668 | 8 | 9.0 |

The MTBE standard sample concentration curve can be established from the data shown in Table 1, as shown in FIG. 2, wherein x axis represents the concentration of the standard sample solution, y axis represents the standard sample solution PID reading obtained by detection, and the following standard sample concentration curve equations are obtained as: $y=5.7561x+1.8626$, $R^2=0.9971$.

Upon detecting the MTBE concentration in the to-be-detected water body, an actual MTBE concentration in the to-be-detected water body can be determined by the standard sample concentration curve equations according to the PID reading obtained by detecting the to-be-detected water body.

Detection Example 2

The device may be used to detect various VOCs. In this example, the same method and device in Detection Example 1 are used to detect specific contents of benzene, tetrachloroethylene, trichloroethylene, vinyl acetate and isooctane in the water respectively, and corresponding standard sample concentration curves are drawn. Detection results of these VOCs are listed in the following Table 2:

TABLE 2

| | Conc. µg/L | Reading (PID reading) | | | | STDEV, % | ppb/(µg/L) |
|---|---|---|---|---|---|---|---|
| | | Test 1 | Test 2 | Test 3 | average | | |
| benzene | 0 | 0 | 0 | 0 | 0 | — | — |
| | 7.4 | 165 | 248 | 234 | 216 | 45 | 29.1 |
| | 37 | 1189 | 1278 | 1311 | 1259 | 63 | 34.0 |
| | 185 | 5218 | 5098 | 5713 | 5343 | 326 | 28.9 |
| | 738 | 16235 | 17823 | 16562 | 16873 | 839 | 22.9 |
| tetrachloroethylene (PCE) | 0 | 0 | 0 | 0 | 0 | — | — |
| | 7.4 | 22 | 27 | 32 | 27 | 5 | 3.7 |
| | 37 | 144 | 157 | 165 | 155 | 10 | 4.2 |
| | 185 | 556 | 575 | 577 | 570 | 11 | 3.1 |
| | 738 | 2867 | 2861 | 2897 | 2875 | 19 | 3.9 |
| trichloroethylene (TCE) | 0 | 0 | 0 | 0 | 0 | — | — |
| | 7.4 | 89 | 75 | 80 | 81 | 7 | 11.0 |
| | 37 | 506 | 426 | 444 | 459 | 42 | 12.4 |
| | 185 | 2257 | 2006 | 1833 | 2032 | 213 | 11.0 |
| | 738 | 7323 | 5029 | 6240 | 6197 | 1148 | 8.4 |
| isooctane | 0 | 0 | 0 | 0 | 0 | — | — |
| | 7.4 | 9 | 9 | 15 | 11 | 4 | 1.5 |
| | 37 | 15 | 30 | 42 | 29 | 14 | 0.8 |
| | 185 | 73 | 84 | 112 | 90 | 20 | 0.5 |
| | 738 | 308 | 262 | 388 | 319 | 64 | 0.4 | detection results show that the PID reading (namely, VOC concentration in the gas) is in a very good correspondence relationship to the VOC concentration in water, and respective concentration detection results also exhibit very good linear relationship (in the table, Conc. µg/L is the concentration of the standard sample solution). The device even The standard sample concentration curves of VOCs can be established from the data shown in Table 2, as shown in FIG. 3. It can be seen from FIG. 3 that detection sensitivity varies with different VOCs. When the types of VOCs in the water are known, conversion may be performed according to the previously-obtained coefficient corresponding to the VOCs. When exact types of VOCs are unknown, the detection result is an approximate total amount of VOCs.

Detection Example 3

The device may quickly in-situ detect the approximate total amount of many VOCs in the water. In this example, the same method and device as in Detection Example 1 are used to detect the total amount of VOCs at different testing points in the wild river water, the specific location is in the vicinity of a sewage drainage outlet of a certain essence factory at a certain river segment, in-situ detection is performed in the river 2 m away from the banks respectively at 10 m upstream of the sewage drainage outlet, 10 m, 50 m and 200 m downstream of the sewage discharge outlet, and each test only needs 2-5 minutes to obtain the detection results. The detection results are listed in the following Table 3:

TABLE 3

| | Position | | | | |
|---|---|---|---|---|---|
| | Pure water | 10 m up-stream | 10 m down-stream | 50 m down-stream | 200 m down-stream |
| PID reading, ppb | 0 | 253 | 910 | 762 | 587 |
| VOC concentration*, μg/L | 0 | 28 | 101 | 85 | 65 |

*VOC concentration in water as calculated by taking MTBE as a standard, 9.0 ppb = 1 μg/L.

Data in Table 3 indicate that the device can quickly in-situ detect the total amount of VOCs in the water that might be polluted and it is of a great practical value for routinely and randomly monitoring of pollution, and in-situ quick detection and evaluation of water pollution conditions in the case of water pollution and dangerous article diffusion caused by sudden events such as chemical substance leakage or crude petroleum oil leakage.

In conclusion, the device of sampling and detecting the volatile organic compounds in the water according to the present invention effectively overcomes the drawbacks in the prior art and exhibits a high utilization value in the industry.

The above embodiments only exemplarily illustrate the principles and effects of the present invention and are not intended to limit the present invention. Those skilled in the art may modify or change the above embodiments without departing from the spirit and scope of the present invention. Hence, all equivalent modifications or variations made by those having ordinary skill in the art without departing from the spirit and technical ideas of the present invention should still be covered by claims of the present invention.

What is claimed is:

1. A sampling and detection device for detecting volatile organic content in water, comprising:
    a hollow sampler wherein a side wall of a lower half of the hollow sampler is provided with more than one water inlet channel, and wherein a lower end of the sampler is provided with a gas bubbler;
    a gas detector connected to the sampler;
    a gas inlet pipe; and
    a purge gas purifier;
    a purge gas intake pump, wherein an end of the gas inlet pipe is in fluid communication with a bottom of the sampler and the other end is fluid coupled to the purge gas intake pump, wherein the gas detector is further coupled with the purge gas intake pump, and wherein the gas inlet pipe is further coupled with the purge gas purifier between the gas detector and the hollow sampler.

2. The sampling and detection device for detecting volatile organic content in water according to claim 1, further comprising:
    a gas outlet pipe, wherein one end of the gas outlet pipe is coupled to a top of the hollow sampler and the other end is coupled to the gas detector.

3. The sampling and detection device for detecting volatile organic content in water according to claim 2, wherein the gas outlet pipe is coupled to a gas sample collection pump.

4. The sampling and detection device for detecting volatile organic content in water according to claim 2, wherein the gas inlet pipe is further coupled with the purge gas purifier; and wherein the gas outlet pipe is coupled with a gas sample dehumidifier.

5. The sampling and detection device for detecting volatile organic content in water according to claim 2, wherein the gas bubbler is disposed at a location where the gas inlet pipe is coupled with the hollow sampler.

6. The sampling and detection device for detecting volatile organic content in water according to claim 1, wherein the water inlet channel comprises one of a pore or a slit, wherein the pore has a diameter between 0.1-5 mm, and the slit is between 0.1-1000 mm long and 0.1-5 mm wide.

7. The sampling and detection device for detecting volatile organic content in water according to claim 1, wherein the selected portion of the hollow sampler is in a range of 3-100 cm high.

8. The sampling and detection device for detecting volatile organic content in water according to claim 1, wherein the gas detector is selected from a group consisting of: a photoionization detector, a thermal conductivity detector, a hydrogen flame detector, an ion mobility detector, a mass spectrometry detector, and a spectral detector.

9. The sampling and detection device for detecting volatile organic content in water according to claim 1, wherein at least one float is further provided on an outer wall of another portion of the hollow sampler.

10. The sampling and detection device for detecting volatile organic content in water according to claim 9, wherein the hollow sampler comprises a hollow column-shaped cavity, wherein the at least one float is coupled to a horizontal section of the column-shaped cavity structure, wherein the cross-sectional area of the column-shaped cavity is between 1 $cm^2$-1 $m^2$, and a ratio of a height of a lower portion of the hollow sampler below the at least one float to a total height of the hollow sampler is in a range of ¼-9/10.

11. The sampling and detection device for detecting volatile organic content in water according to claim 1, wherein the gas detector is further coupled to the purge gas intake pump, and wherein a closed loop is formed between the gas inlet pipe, the hollow sampler, a gas outlet pipe, and the gas detector.

12. The sampling and detection device for detecting volatile organic content in water according to claim 11, wherein the purge gas intake pump is a gas pump carried in the gas detector.

13. A method for detecting volatile organic content in water, the method comprising:
    placing a sampler in a to-be-detected water body, a side wall of a selected portion of the sampler is provided with more than one water inlet channel, and wherein an end of the sampler is provided with a gas bubbler;

introducing water into the sampler through the more than one water inlet channel;

introducing a purge gas into the hollow sampler;

passing the purge gas through the water in the hollow sampler and then into a gas detector for detection, wherein the purge gas flow rate passing into the hollow sampler is controlled to be greater than the purge gas flow rate passing out of the hollow sampler and into the gas detector; and obtaining concentration of volatile organic compounds in the to-be-detected water body according to detection results obtained by the gas detector and a standard sample concentration curve.

14. The method for detecting volatile organic content in water according to claim 13, wherein placing the sampler in the to-be-detected water body includes using a purge gas intake pump to introduce the purge gas into the sampler via the inlet pipe, and then via a gas outlet pipe into the gas detector for detection.

15. The method for detecting volatile organic content in water according to claim 14, wherein the purge gas flow of the gas inlet pipe is a predetermined amount greater than or equal to the purge gas flow in the gas outlet pipe.

16. The method for detecting volatile organic content in water according to claim 14, which includes setting a gas flow in the gas inlet pipe in a range of 1 ml/min-10 L/min, and setting a volume of the water entering the sampler in a range of 1 ml-1000 L.

17. The method for detecting volatile organic content in water according to claim 13, wherein the purge gas is selected from a gas which includes at least one of nitrogen, air, and inert gases.

18. A sampling and detection device for detecting volatile organic content in water comprising:

the water;

a hollow sampler, wherein at least a portion of the hollow sampler is submerged in the water, wherein the hollow sampler defines a gas sample collection chamber, and wherein a side wall of a lower half of the hollow sampler is provided with more than one water inlet channel; and a gas detector coupled to the hollow sampler, wherein a side wall of a portion of the hollow sampler defines at least one water inlet channel, wherein a gas bubbler is coupled to the hollow sampler, wherein the hollow sampler is coupled to the gas detector by a closed loop gas flow system, wherein the closed loop includes an intake pump and a gas sample collection pump, wherein the intake pump and gas sample collection pump are separate pumps, and wherein the gas detector is at least one of a photoionization detector (PID), a thermal conductivity detector (TCD), a hydrogen flame detector, an ion mobility detector, a mass spectrometry detector, or a spectral detector.

\* \* \* \* \*

UNITED STATES PATENT AND TRADEMARK OFFICE
CERTIFICATE OF CORRECTION

PATENT NO.        : 9,983,182 B2
APPLICATION NO.   : 14/395576
DATED             : May 29, 2018
INVENTOR(S)       : Bing Chen and Qian Zheng Page 1 of 1

It is certified that error appears in the above-identified patent and that said Letters Patent is hereby corrected as shown below:

On the Title Page

Item (74), Line 2: insert --,-- after "Martin"

Page 2, Item (56), OTHER PUBLICATIONS, Line 1: "EP138095542" should be "EP13809554.2"

Signed and Sealed this
Fourteenth Day of August, 2018

Andrei Iancu
*Director of the United States Patent and Trademark Office*